United States Patent
Brenneman et al.

[11] Patent Number: 5,916,230
[45] Date of Patent: *Jun. 29, 1999

[54] BLOOD SAMPLING DEVICE WITH ADJUSTABLE END CAP

[75] Inventors: Allen Brenneman, Goshen, Ind.; D. Glenn Purcell, Edwardsburg, Mich.

[73] Assignee: Bayer Corporation, Elkhart, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/876,260

[22] Filed: Jun. 16, 1997

[51] Int. Cl.$^6$ .................................................. A61B 17/32
[52] U.S. Cl. ............................................ 606/172; 606/182
[58] Field of Search ................................... 606/182, 181, 606/183, 172

[56] References Cited

U.S. PATENT DOCUMENTS

| | | | |
|---|---|---|---|
| Re. 32,922 | 5/1989 | Levin et al. | 128/314 |
| 4,442,836 | 4/1984 | Meinecke et al. | 128/314 |
| 4,449,529 | 5/1984 | Burns et al. | 128/314 |
| 4,462,405 | 7/1984 | Ehrlich | 128/329 R |
| 4,517,978 | 5/1985 | Levin et al. | 128/314 |
| 4,553,541 | 11/1985 | Burns | 128/314 |
| 4,653,513 | 3/1987 | Dombrowski | 128/765 |
| 4,858,607 | 8/1989 | Jordan et al. | 128/314 |
| 4,976,724 | 12/1990 | Nieto et al. | 606/182 |
| 5,201,324 | 4/1993 | Swierczek | 128/770 |
| 5,368,047 | 11/1994 | Suzuki et al. | 128/765 |
| 5,554,166 | 9/1996 | Lange et al. | 606/182 |
| 5,613,978 | 3/1997 | Harding | 606/182 |

*Primary Examiner*—Michael H. Thaler
*Attorney, Agent, or Firm*—Roger Norman Coe

[57] ABSTRACT

A blood sampling device (10) is provided with a housing (12), an end cap (60) adapted to be connected to the housing (12), and a lancet (32) which is movable in a lancing direction between a retracted position in which the lancet (32) does not extend outside of the end cap (60) and an extended position in which the lancet (32) is adapted to make a puncture having a depth. The blood sampling device (10) includes an actuator mechanism for causing the lancet (32) to move from the retracted position to the extended position and an attachment mechanism for allowing the end cap (60) to be securely attached to the housing (12) by moving the end cap (60) in a direction parallel to the lancing direction from a removed position in which the end cap (60) is separated from the housing (12) to a secured position in which the end cap (60) is securely attached to the housing (12) and a mechanism for adjusting the puncture depth of the lancet (32).

17 Claims, 1 Drawing Sheet

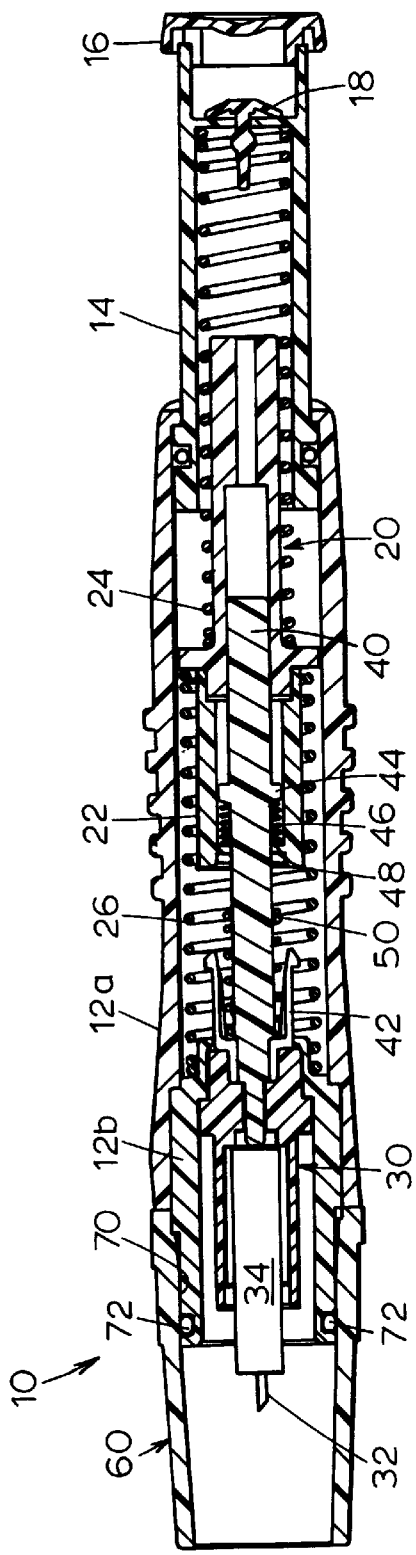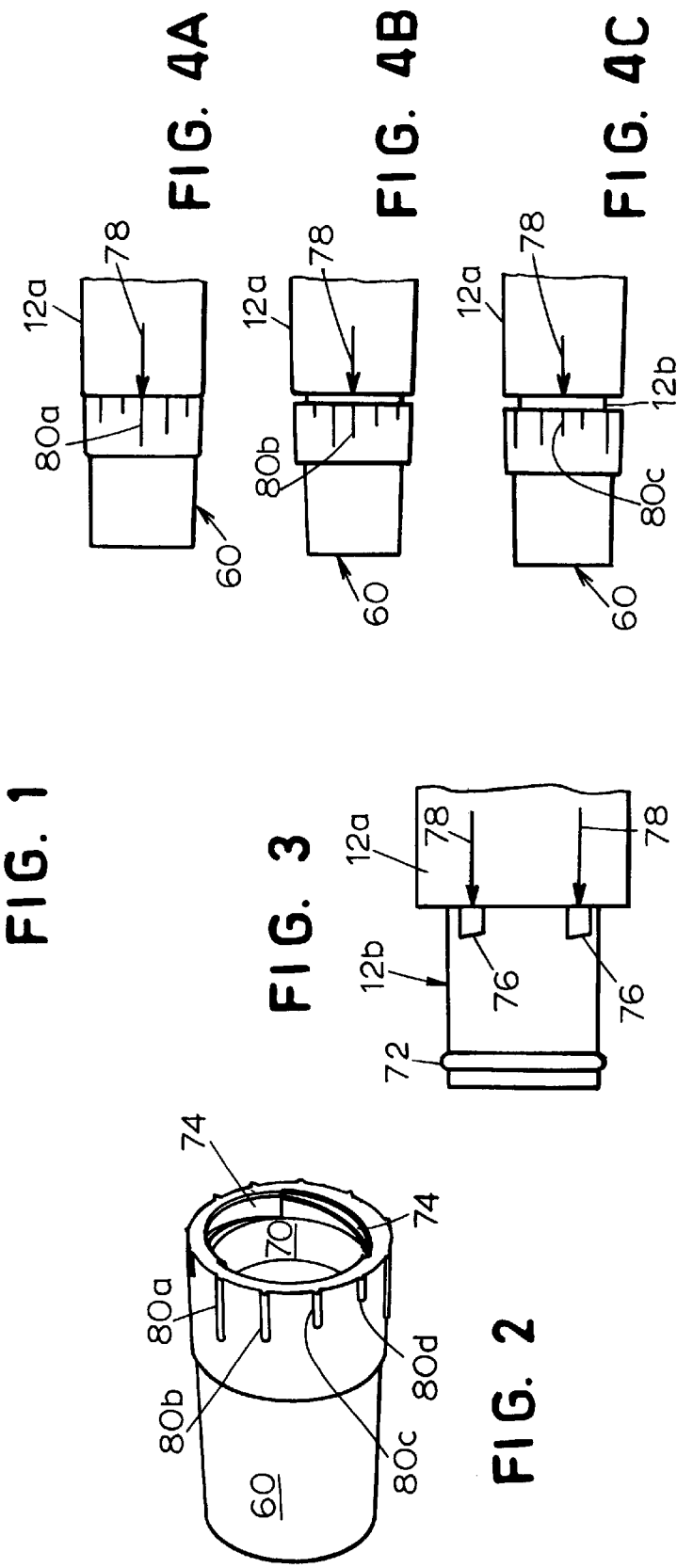

BLOOD SAMPLING DEVICE WITH ADJUSTABLE END CAP

BACKGROUND OF THE INVENTION

The present invention relates to a blood sampling device that incorporates a lancet for piercing the skin and an adjustable end cap for regulating the depth to which the lancet pierces the skin.

Various types of blood sampling devices for drawing a blood sample from a skin puncture made by a lancet have been described. For example, U.S. Pat. No. 5,368,047 to Suzuki, et al. discloses a blood sampling device that has a lancet connected to a spring-loaded plunger that is reciprocable in a cylindrical housing between a retracted position and an extended position. The plunger has a gasket which makes sealing contact with the interior wall of the housing when the plunger is moved from its extended position to its retracted position.

Various mechanisms for adjusting the depth of a puncture made by a blood sampling device have been provided. For example, U.S. Pat. No. 5,554,166 to Lange, et al. discloses a blood lancet device for withdrawing blood that is provided with an adjustable end cap that is threadably coupled to the lancet device. After every use of a blood sampling device, the used lancet is discarded and a new lancet is attached to prevent the spread of communicable diseases. Use of a blood sampling device with a threaded end cap which must be unscrewed from the device in order to change the lancet can be unduly time consuming.

Other conventional methods of adjusting the depth of puncture have included providing a blood sampling device with different-sized frictionally retained unthreaded end caps which may be slid onto the housing of the device in a direction parallel to the lancing direction, such as the blood sampling devices marketed by Bayer Corporation under the trademark "Glucolet." To make a relatively deep puncture with such a device, an end cap having a relatively short length is used, and to make a relatively shallow puncture, an end cap having a relatively long length is used. However, the need to provide multiple end caps with each blood sampling device is not optimal.

SUMMARY OF THE INVENTION

The invention is directed to a blood sampling device having a housing, an end cap adapted to be connected to the housing, and a lancet which is movable in a lancing direction between a retracted position in which the lancet does not extend outside of the end cap and an extended position in which the lancet is adapted to make a puncture having a selected puncture depth. An actuator mechanism is provided in the housing for causing the lancet to move from the retracted position to the extended position. The blood sampling device includes attachment means for allowing the end cap to be securely attached to the housing by moving the end cap in a direction parallel to the lancing direction from a removed position in which the end cap is separated from the housing and in which the end cap may occupy any angular orientation relative to the housing to a secured position in which the end cap is securely attached to the housing. The blood sampling device also includes means for adjusting the puncture depth of the lancet.

The end cap may be provided with a plurality of position marks disposed thereon, each of the position marks being spaced from one another about the periphery of the end cap, and the housing may be provided with a reference mark disposed thereon. The end cap may be rotatable with respect to the housing between a plurality of different angular positions including a first angular position in which a first of the position marks disposed on the end cap is aligned with the reference mark disposed on the housing and a second angular position in which a second of the position marks disposed on the end cap is aligned with the reference mark disposed on the housing. Each of the position marks disposed on the end cap may be provided in the form of a linear mark, each of the linear marks having a different length and corresponding to a different puncture depth.

The attachment means may be provided in the form of frictional retainer means, such as an O-ring disposed on the housing and which makes frictional contact with an interior portion of the end cap. The end cap may be provided with an interior portion with an angled slot, and the housing may be provided with a stop member that makes contact with the angled slot in the end cap, whereby rotation of the end cap relative to the housing causes the stop member of the housing to make contact with a different portion of the angled slot in the end cap to vary the spacing between the end cap and a portion of the housing in a direction parallel to the lancing direction.

The use of an end cap in accordance with the invention is advantageous in that the end cap can be simply slid onto the body of the blood sampling device in a horizontal direction, without any twisting of the end cap, and the depth of the puncture to be made can be adjusted by rotating the end cap a relatively small amount. The end cap in accordance with the invention thus eliminates the need for multiple end caps of different sizes.

These and other features of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 1 is a cross-sectional view of one embodiment of a blood sampling device in accordance with the invention;

FIG. 2 is a perspective view of the end cap of the blood sampling device;

FIG. 3 is a partial side view of one end of the blood sampling device with the end cap removed; and FIGS. 4A through 4C are partial side views of the blood sampling device showing the end cap in different positions.

DETAILED DESCRIPTION OF THE PREFERRED EMBODIMENT

FIG. 1 is a cross-sectional view of a preferred embodiment of a blood sampling device 10 for taking a sample of blood from a person. Referring to FIG. 1, the blood sampling device 10 has a housing composed of a main housing portion 12a and a sleeve 12b fixed to the main housing portion 12a. The blood sampling device 10 has a plunger 14, a portion of which is slidably disposed within the main housing 12a. A button 16 is attached to an end of the plunger 14, and a rubber check valve 18 is supported within the plunger 14.

A spring support member 20 is slidably disposed within the main housing 12a, and a release member 22 is fixed to the spring support 20. A secondary draw spring 24 is disposed around the spring support 20 and within the plunger 14, and a main draw spring 26 is disposed between the spring support member 20 and the sleeve 12b. A movable lancet holder 30 is disposed within the sleeve 12b, and a lancet 32 is supported by a lancet shaft 34 held in a fixed position relative to the movable lancet holder 30.

A shaft 40 and a hook member 42 are connected to the lancet holder 30. The shaft 40 passes through a central bore formed in the release member 22 and extends within a central bore formed in the spring support member 20. The shaft 40 has an annular collar 44, and a return spring 46 is disposed between the collar 44 and an internal shoulder 48 formed in the release member 22. A shoot spring 50 is disposed around the shaft 40 and is supported between the hook member 42 and the release member 22. An end cap 60 is supported by the sleeve 12b.

To use the blood sampling device 10, the end cap 60 is placed against the skin, and the button 16 is pushed towards the main housing 12a, or leftwardly as shown in FIG. 1. The leftward movement of the button 16 and plunger 14 will cause the draw springs 24, 26 to compress and the spring support member 20 and the release member 22 to move leftward. As the release member 22 moves leftward, the return spring 46 will become uncompressed and the release member 22 will make contact with the right end of the shoot spring 50. Further leftward movement of the release member 22 after it makes contact with the shoot spring 50 will cause the hook member 42 and the lancet holder 30 to move leftward, until the outwardly spread arms of the hook member 42 engage the rightmost surface of the sleeve 12b.

After such engagement is made, further movement of the release member 22 will cause the annular edge of the release member 22 to contact, and then push inwardly, the outwardly spread arms of the hook member 42. When the arms have been pushed inwardly to such an extent that they no longer make contact with the rightmost annular surface of the sleeve 12b (which has a central bore disposed therein), the compressed shoot spring 50 causes the lancet 32 (and the lancet holder 30 and hook member 42) to be shot leftwardly to a point beyond the left-hand edge of the end cap 60 to puncture the skin. After the puncture is made, the return spring 46 causes the lancet 32 to be retracted back within the end cap 60. During such retraction, the O-ring 72 helps facilitate the formation of a partial vacuum within the blood sampling device 10, which causes blood from the puncture made by the lancet 32 to be drawn into the end cap 60.

The end cap 60 may be made of transparent plastic having a frosted portion adjacent the lancet 32 to prevent the user from seeing the lancet 32 prior to using the blood sampling device 10. The transparent plastic allows the user to view the amount of blood that has collected within the end cap 60 after the puncture is made to that one can determine whether or not enough blood has been drawn in order to conduct a measurement.

The specific actuating structure for causing the lancet 32 to move between its retracted and extended positions as described above is conventional, and a blood sampling device incorporating that actuating structure is commercially available from Bayer Corporation. Many different types of actuating structures other than the above structure could be used in the invention.

After a puncture is made, the end cap 60 is removed from the sleeve 12b, and the lancet 32 and lancet shaft 34 are removed and discarded. Before another puncture is made, a new lancet 32 and lancet shaft 34 are inserted into the sleeve 12b. The efficient removal and replacement of the end cap 60 is facilitated by the manner in which it is connectable to the sleeve 12b. Referring to FIGS. 1 and 2, the interior portion of the end cap 60 has a smooth, unthreaded interior surface 70, and the end cap 60 is held securely onto the sleeve 12b by frictional contact between that surface 70 and a rubber O-ring 72 disposed around the end of the sleeve 12b. Due to that frictional contact, the end cap 60 can be removed by simply pulling it off the sleeve 12b in a direction parallel to the direction in which the lancet 32 moves (i.e., horizontal in FIG. 1).

The interior portion of the end cap 60 has a plurality of angled slots 74 (FIG. 2) formed therein which are adapted to mate with a like number of stop members 76 (FIG. 3) formed on the outer periphery of the sleeve 12b, each of the stop members 76 being aligned with a respective reference mark 78 disposed on the exterior of the main housing portion 12a.

As shown in FIG. 2, the end cap 60 has a plurality of sets of positions marks 80 disposed thereon, each set including a relatively long position mark 80a and three additional position marks 80b–80d, each of which is successively shorter in length.

To place the end cap 60 onto the sleeve 12b, the end cap 60 is simply moved or slid, with the end cap 60 in any angular orientation relative to the sleeve 12b, in a horizontal direction towards the main housing 12a until the stop members 76 make contact with the leftmost portions of the angled slots 74. When such contact is made, the depth of the puncture to be made can be adjusted by rotating the end cap 60 until one of the position marks 80 disposed on the end cap 60 is aligned relative to one of the reference markers 78 disposed on the main housing 12a.

Referring to FIG. 4A, to make a relatively deep puncture, the end cap 60 is rotated until the longest position mark 80a on the end cap 60 is aligned with one of the reference marks 78 on the housing. Referring to FIG. 4B, the puncture depth can be reduced by twisting the end cap 60 so that the reference mark 78 on the main housing 12a is aligned with the position mark 80b. Twisting of the end cap 60 from its position shown in FIG. 4A to its position shown in FIG. 4B will cause the stop members 76 (FIG. 3) to force the end cap 60 away from the main housing portion 12a due to each of the stop members 76 making contact with a shallower portion of the angled slots 74 (FIG. 2) formed in the interior of the end cap 60.

In a similar manner, the end cap 60 can be twisted to a position shown in FIG. 4C in which the position mark 80c on the end cap 60 is aligned with one of the reference marks 78 on the main housing 12a. It should be noted that the length of each of the position marks 80a–80d corresponds to the length of the puncture that would be made with the end cap 60 in that position. For example, alignment of the reference mark 78 with the relatively short position mark 80c as shown in FIG. 4C would result in a relatively shallow puncture since the end cap 60 is spaced relatively far from the main housing 12a and since the lancet 32 would not extend as far beyond the leftmost edge of the end cap 60.

Although FIGS. 4A and 4C show the reference mark 78 on the housing 12a to be aligned with one of the positions marks 80, it should be noted that the puncture depth can continuously adjusted in a very precise manner by aligning the reference mark 78 so that it is positioned between adjacent position marks 80. Because there are multiple sets of position markers 80 on the end cap 60, the end cap 60 does not have to be rotated very much after it is slid onto the device 10 to obtain desired alignment of the reference marker 78 with one of the position markers 80.

Once the end cap 60 is slid onto the device 10 and adjusted, pressing the device 10 against the skin does not alter the position of the end cap 60 since the end cap 60 is held on the device 10 tightly.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A blood sampling device, comprising:

a housing (12) having a reference mark (78) disposed thereon;

an end cap (60) adapted to be connected to said housing (12), said end cap (60) having a plurality of position marks (80) disposed thereon, each of said position marks (80) being spaced from one another about the periphery of said end cap (60);

a lancet (32) which is movable in a lancing direction between a retracted position in which said lancet (32) does not extend outside of said end cap (60) and an extended position; and an actuator mechanism disposed in said housing (12) for causing said lancet (32) to move from said retracted position to said extended position, said end cap (60) being rotatable with respect to said housing (12) between a plurality of different angular positions including a first angular position in which a first of said position marks (80) disposed on said end cap (60) is aligned with said reference mark (78) disposed on said housing (12) and a second angular position in which a second of said position marks (80) disposed on said end cap (60) is aligned with said reference mark (78) disposed on said housing (12), said end cap (60) being adapted to slide onto said housing (12) in a direction parallel to said lancing direction from a removed position in which said end cap (60) is separated from said housing (12) and in which said end cap (60) may occupy any angular orientation relative to said housing (12) to a secured position in which said end cap (60) is securely attached to said housing (12), wherein said end cap (60) has an internal periphery and wherein said blood sampling device additionally comprises a plurality of angled slots (74) disposed about the entire internal periphery of said end cap (60).

2. A blood sampling device as defined in claim 1 wherein said end cap (60) is securely attached to said housing (12) by frictional retainer means.

3. A blood sampling device as defined in claim 2 wherein said frictional retainer means comprises an O-ring (72) disposed on said housing (12), said O-ring (72) making frictional contact with an interior portion of said end cap (60).

4. A blood sampling device as defined in claim 1 wherein each of said position marks (80) disposed on said end cap (60) comprises a linear mark, each of said linear marks having a different length.

5. A blood sampling device as defined in claim 1 wherein each of said position marks (80) disposed on said end cap (60) comprises a linear mark having a different length, each of said lengths corresponding to a different puncture depth.

6. A blood sampling device, comprising:

a housing (12) having a reference mark (78) disposed thereon;

an end cap (60) adapted to be connected to said housing (12), said end cap (60) having a plurality of position marks (80) disposed thereon, each of said position marks (80) being spaced from one another about the periphery of said end cap (60);

a lancet (32) which is movable in a lancing direction between a retracted position in which said lancet (32) does not extend outside of said end cap (60) and an extended position; and an actuator mechanism disposed in said housing (12) for causing said lancet (32) to move from said retracted position to said extended position, said end cap (60) being rotatable with respect to said housing (12) between a plurality of different angular positions including a first angular position in which a first of said position marks (80) disposed on said end cap (60) is aligned with said reference mark (78) disposed on said housing (12) and a second angular position in which a second of said position marks (80) disposed on said end cap (60) is aligned with said reference mark (78) disposed on said housing (12), said end cap (60) being adapted to slide directly onto said housing (12) without angular rotation of said end cap (60) relative to said housing (12) in a direction parallel to said lancing direction from a removed position in which said end cap (60) is separated from said housing (12) and in which said end cap (60) may occupy any angular orientation relative to said housing (12) to a secured position in which said end cap (60) is securely attached to said housing (12), said end cap (60) having an interior portion with an angled slot (74) disposed within said interior portion, wherein said end cap (60) has an internal periphery and wherein said blood sampling device additionally comprises a plurality of angled slots (74) disposed about the internal periphery of said end cap (60).

7. A blood sampling device as defined in claim 6 wherein said end cap (60) is securely attached to said housing (12) by frictional retainer means.

8. A blood sampling device as defined in claim 7 wherein said frictional retainer means comprises an O-ring (72) disposed on said housing (12), said O-ring (72) making frictional contact with an interior portion of said end cap (60).

9. A blood sampling device as defined in claim 6 wherein each of said position marks (80) disposed on said end cap (60) comprises a linear mark, each of said linear marks having a different length.

10. A blood sampling device as defined in claim 6 wherein each of said position marks (80) disposed on said end cap (60) comprises a linear mark having a different length, each of said lengths corresponding to a different puncture depth.

11. A blood sampling device, comprising:

a housing (12);

an end cap (60) adapted to be connected to said housing (12);

a lancet (32) which is movable in a lancing direction between a retracted position in which said lancet (32) does not extend outside of said end cap (60) and an extended position in which said lancet (32) is adapted to make a puncture having a depth;

an actuator mechanism disposed in said housing (12) for causing said lancet (32) to move from said retracted position to said extended position;

attachment means for allowing said end cap (60) to be securely attached to said housing (12) by moving said end cap (60), without rotation of said end cap (60) relative to said housing (12), in a direction parallel to said lancing direction from a removed position in which said end cap (60) is separated from said housing (12) and in which said end cap (60) may occupy any angular orientation relative to said housing (12) to a secured position in which said end cap (60) is securely attached to said housing (12); and means for adjusting said puncture depth of said lancet (32), said adjusting means comprising a plurality of angled slots (74) disposed about an internal periphery of said end cap (60).

12. A blood sampling device as defined in claim 11 wherein said end cap (60) has a plurality of position marks (80) disposed thereon, each of said position marks (80) being spaced from one another about the periphery of said end cap (60).

13. A blood sampling device as defined in claim 12 wherein said housing (12) has a reference mark (78) disposed thereon and wherein said end cap (60) is rotatable with respect to said housing (12) between a plurality of different angular positions including a first angular position in which a first of said position marks (80) disposed on said end cap (60) is aligned with said reference mark (78) disposed on said housing (12) and a second angular position in which a second of said position marks (80) disposed on said end cap (60) is aligned with said reference mark (78) disposed on said housing (12).

14. A blood sampling device as defined in claim 13 wherein each of said position marks (80) disposed on said end cap (60) comprises a linear mark, each of said linear marks having a different length.

15. A blood sampling device as defined in claim 13 wherein each of said position marks (80) disposed on said end cap (60) comprises a linear mark having a different length, each of said lengths corresponding to a different puncture depth.

16. A blood sampling device as defined in claim 11 wherein said attachment means comprises frictional retainer means.

17. A blood sampling device as defined in claim 16 wherein said frictional retainer means comprises an O-ring (72) disposed on said housing (12), said O-ring making frictional contact with an interior portion of said end cap (60).

* * * * *